United States Patent [19]
Levine

[11] Patent Number: 5,858,669
[45] Date of Patent: Jan. 12, 1999

[54] BECLIN, A NOVEL BCL-2 INTERACTING GENE NEAR BRCA1 ON CHROMOSOME 17Q21 AND METHODS OF USE

[75] Inventor: Beth Cindy Levine, Scarborough, N.Y.

[73] Assignee: The Trustees of Columbia University in the City of New York, New York, N.Y.

[21] Appl. No.: 712,939

[22] Filed: Sep. 13, 1996

[51] Int. Cl.$^6$ ....................................................... C12Q 1/68
[52] U.S. Cl. .................................. 435/6; 935/77; 935/78
[58] Field of Search .............................. 435/6, 91.2, 91.1, 435/174; 536/23.1, 24.3, 24.33, 26.6, 333; 530/350

[56] References Cited

PUBLICATIONS

Reed et al. J. of Cellular Biochemistry 60:23–32, 1996.
Nora, In Medical Genetics: Principles and Practice, ch 7, Lea & Febiger, Phil pp. 120–129, 1989.
Cropp, C.S. et al. (1993) *Cancer Res.* 53: 5617–5619.
Eccles, D.M., et al. (1992) *Oncogene* 7: 2069–2072.
Friedman, L.S., et al. (1995) *Genomics* 25: 256–263.
Futreal, P.A., et al. (1994) *Science* 266: 120–122.
Futreal, P.A., et al. (1992) *Cancer Res.* 52: 2624–2627.
Hosking, L., et al. (1995) *Nature Genet* 9: 343–344.
Levine, B., et al. (1993) *Nature* 361: 739–742.
Merajver, S.D., et al. (1995) *Nature Genet.* 9: 439–443.
Rommens, J. M., et al. (1995) *Genomics* 28: 530–542.
Saito, H., et al. (1993) *Cancer Res.* 53: 3382–3385.
Sato, T., et al. (1994) 91: 9238–9242.
Takhashi, H., et al. (1995) *Cancer Res.* 55: 2998–3002.
Tangir, J., et al. (1996) *Oncogene* 12: 735–740.
Yang–Feng, et al. (1993) *Int. J. Cancer* 54: 546–551.

*Primary Examiner*—Lisa B. Arthur
*Attorney, Agent, or Firm*—John P. White; Cooper & Dunham LLP

[57] ABSTRACT

This invention provides for an isolated nucleic acid which encodes a wildtype human Beclin and a mutant human Beclin. This invention also provides a vector containing the isolated nucleic acid which encodes a wildtype human Beclin. This invention also provides for a method of producing a wildtype human Beclin. This invention also provides for a purified, wildtype human Beclin. This invention also provides for a method for determining whether a subject has a predisposition for cancer. This invention also provides a method for determining whether a subject has cancer. This invention also provides for a method for inhibiting cell proliferation in cells unable to regulate themselves. This invention also provides for a method for treating a subject who has cancer. This invention also provides a pharmaceutical composition composed of the wildtype human Beclin. This invention also provides a method for detecting a mutant human Beclin in a subject. This invention also provides a method for treating a subject unable to control apoptosis in the cells of the subject.

8 Claims, 7 Drawing Sheets

```
ATGGAAGGGT CTAAGACGTC CAACAACAGC ACCATGCAGG TGAGCTTCGT GTGCCAGCGC TGCAGCCAGC CCCTGAAACT GGACACGAGT      90
 M  E  G  S  K  T  S  N  N  S  T  M  Q  V  S  F  V  C  Q  R  C  S  Q  P  L  K  L  D  T  S           30

TTCAAGATCC TGGACCGTGT CACCATCCAG GAACTCACAG CTCCATTACT TACCACAGCC CAGGCGAAAC CAGGAGAGAC CCAGGAGGAA     180
 F  K  I  L  D  R  V  T  I  Q  E  L  T  A  P  L  L  T  T  A  Q  A  K  P  G  E  T  Q  E  E          60

GAGACTAACT CAGGAGAGGA GCCATTTATT GAAACTCCTC GCCAGGATGG TGTCTCTCGC AGATTCATCC CCCCAGCCAG GATGATGTCC     270
 E  T  N  S  G  E  E  P  F  I  E  T  P  R  Q  D  G  V  S  R  R  F  I  P  P  A  R  M  M  S          90

ACAGAAAGTG CCAACAGCTT CACTCTGATT GGGGAGTAT CTGATGGCGG CACCATGGAG AACCTCAGCC GAAGACTGAA GGTCACTGGG     360
 T  E  S  A  N  S  F  T  L  I  G  E  V  S  D  G  G  T  M  E  N  L  S  R  R  L  K  V  T  G         120

GACCTTTTTG ACATCATGTC GGGCCAGACA GATGTGGATC ACCCACTCTG TGAGGAATGC ACAGATACTC TTTTAGACCA GCTGGACACT     450
 D  L  F  D  I  M  S  G  Q  T  D  V  D  H  P  L  C  E  E  C  T  D  T  L  L  D  Q  L  D  T         150

CAGCTCAACG TCACTGAAAA TGAGTGTCAG AACTACAAAC GCTGTTTGGA GATCTTAGAG CAAATGAATG AGGATGACAG TGAACAGTTA     540
 Q  L  N  V  T  E  N  E  C  Q  N  Y  K  R  C  L  E  I  L  E  Q  M  N  E  D  D  S  E  Q  L         180

CAGATGGAGC TAAAGGAGCT GGCACTAGAG TGATCCTATGC AGGAGGAAGC GCTGGAAGAC GTGGAAAAGA ACCGCAAGAT AGTGGCAGAA     630
 Q  M  E  L  K  E  L  A  L  E  *  S  Y  A  G  G  S  A  G  R  G  K  T  T  A  T  A  S  A  E         210

AATCTCGAGA AGGTCCAGGC TGAGGCTGAG AGACTGGATC AGGAGGAAGC AGGAGGAAGC TCAGTATCAG AGAGAATACA GTGAATTTAA     720
 N  L  E  K  V  Q  A  E  A  E  R  L  D  Q  E  E  A  E  E  A  Q  Y  Q  R  E  Y  S  E  F  K         240

CTGGAGCTGG ATGATGAGCT TCCACATCTG GAAGAGTGTT GAAAAACCAGA CAGTTTGGCA TGCGTTATGC CCAGACGCAG GGTCGCCTGC     810
 L  E  L  D  D  E  L  K  S  V  E  N  Q  M  R  Y  A  Q  T  Q  L  D  K  L                           270

AATGAGATTA ATGCTGCTTG GGGCCAGACT GTGTTGCTGC CAGTTTGGCA CAATCAATAA CTTCAGGCTG GGCCAATAAG AATTTCAGAG     900
 N  E  I  N  A  A  W  G  Q  T  V  L  L  L  Q  F  G  T  I  N  N  F  R  L  A  N  K  F  Q  R         300

GTTCCTTACG GAAACCATTC ATATCTGGAG TCTCTGACAG ACAAATCTAA TCCATGCTCT ACAAATCTAA GGAGCTGCCG TTATACTGTT     990
 V  P  Y  G  N  H  S  Y  L  E  S  L  T  D  K  S  K  E  L  P  L  Y  C  S                           330

TGGGACAACA AGTTTGACCA TGCAATGGTG GCTTTCCTGG ACTGTGTGCA GCAGTTTCAA AGAGAGGTTG AGAAAGGCGA GACACGTTTT    1080
 W  D  N  K  F  D  H  A  M  V  A  F  L  D  C  V  Q  Q  F  K  E  E  V  E  K  G  E  T  R  F         360

TGTCTTCCCT ACAGGATGGA TGTGGAGAAA GGCAAGATTG AAGACACAGG AGGCAGTGGC GGCTCCTATT CCATCAAAAC CCAGTTTAAC    1170
 C  L  P  Y  R  M  D  V  E  K  G  K  I  E  D  T  G  G  S  G  S  Y  S  I  K  T  Q  F  N           390

TCTGAGGAGC AGTGGACAAA AGCTCTCAAG TTCATGCTGA CGAATCTTAA GCTTGGGTGT CCTCACAATT TTATAACAAA               1260
 S  E  E  Q  W  T  K  A  L  K  F  M  L  T  N  L  K  A  W  V  S  Q  F                              420

TGA                                                                                                 1353
 *                                                                                                   451
```

5,858,669

BECLIN, A NOVEL BCL-2 INTERACTING GENE NEAR BRCA1 ON CHROMOSOME 17Q21 AND METHODS OF USE

The invention disclosed herein was made with Government support under Grant No. K08AI01217-01 from the National Institutes Of Health of the United States Department of Health and Human Services. Accordingly, the U.S. Government has certain rights in this invention.

BACKGROUND

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

A. Regulation of Apoptosis

1. Apoptosis is important in diverse physiologic processes; the abnormal regulation of apoptosis is important in diverse pathologic processes, including turmorigenesis.

Apoptosis is a highly conserved innate mechanism by which mammalian cells commit suicide. This mechanism allows an organism to eliminate unwanted or defective cells by an orderly process of cellular disintegration, and is characterized by certain stereotypic biochemical (e.g. endonucleosomal cleavage into 180–200 bp multimers) and morphologic features (e.g. chromatin condensation, cytoplasmic blebbing, etc.). Apoptosis plays a role in physiologic processes such as differentiation during embryogenesis, establishment of immune self-tolerance, and killing of cytotoxic immune cells, and apoptosis can be induced in response to a variety of stimuli including DNA damage, growth factor withdrawal, $Ca^{2+}$ influx, ischemia, and viral infection. The unwanted occurrence of apoptosis may play a role in neurodegenerative diseases and aging, and the diminution of apoptotic death may play a role in cancer and chemoresistance.

2. Apoptosis and the cell cycle may share common pathways.

In recent years, the concept that the cell cycle and apoptosis are inextricably linked has gained widespread support in the cell death field. Several different lines of evidence support this concept. For example, in response to different death signals, normally quiescent cells express elevated levels of cell cycle genes (Buttyan, 1991; Freeman, 1994). Oncogenes such as c-myc (Evan, et al., 1996), ras (Wyllie, et al., 1987; Tanaka, et al., 1994) and adenovirus ELA (White, 1991), that promote cell proliferation, also act as triggers of apoptosis. Loss of normal restraints at the Gl checkpoint, such as inactivation of the retinoblastoma gene product, p105Rb (Clarke, et al, 1992; Lee, et al 1992; Jacks, et al, 1992), or deregulated expression of the Gl-specific E2F transcription factors (Shan, et al., 1994; Qin, et al., 1994; Wu, et al., 1994) results in uncontrolled proliferation and apoptosis. Loss of the p53 tumor suppressor gene results in resistance to certain apoptotic triggers, and p53 overexpression induces some types of apoptosis (reviewed in Evan, 1995). The morphologic features of apoptosis resemble those of mitotic catastrophe (reviewed in King and Cidlowski, 1995), and premature activation of cyclin dependent kinases is required for some forms of apoptosis (Shi, et al., 1994). Furthermore, several agents that block cell cycle progression also protect neuronal cells from apoptosis induced by withdrawal of trophic factor support (Farinelli and Greene, 1996) and T lymphocytes form apoptosis induced by T-cell receptor ligation (Boehme and Lenardo, 1993). These observations all support the notion of a link between the cell cycle and apoptosis.

3. An evolutionarily conserved set of cellular genes regulate apoptosis.

Several mammalian genes have been identified that function as either inducers (e.g. faslapo-1, bax, ICE-like cysteine proteases, p53) or repressors (e.g. bcl-2, bcl-$x_s$, bcl-$x_L$) of an evolutionarily conserved apoptotic death pathway. Prevailing hypotheses in the cell death field are that a family of ICE-like cysteine proteases (CED-3, ICE, Nedd-2/ICH-1, CPP32) constitute the pivotal triggers of both nematode and mammalian cell suicide program and that a family of bcl-2 related genes constitute the final downstream negative regulators of cell death. Despite the identification of several effectors and repressors of cell death, the precise molecular mechanisms underlining the action of each of these genes remains poorly defined.

4. Bcl-2, the proto-oncogene, inhibits a variety of types of apoptosis.

Bcl-2 (for B cell lymphoma 2) is the prototypic anti-apoptotic gene. It was first discovered by virtue of its involvement in the t(14:18) chromosomal translocations found in the majority of non-Hodgkin's B cell lymphomas (Tsujimoto and Croce, 1985). Bcl-2 can prevent or delay apoptosis induced by a wide variety of stimuli (reviewed in Park and Hockenbery, 1996), including growth factor deprivation, alterations in $Ca^{2+}$, free radicals, cytoxic lymphokines. some types of viruses, radiation and most chemotherapeutic drugs. The ability of Bcl-2 to inhibit apoptosis induced by such diverse stimuli suggests that this oncoprotein controls a common final pathway involved in cell death regulation.

5. Dysregulated Bcl-2 expression occurs in a wide variety of human cancers and contributes to neoplastic cell expansion.

While the bcl-2 gene was first discovered because of its involvement in t(14:18) translocations found frequently in non-Hodgkin's lymphomas, high levels and aberrant patterns of bcl-2 gene expression have been reported in a wide variety of human cancers, including colorectal, gastric, prostate, non-small cell lung, neuroblastomas, breast and ovarian cancer (reviewed in Reed, et al., 1996). In these tumors, it is thought that Bcl-2 contributes to neoplastic cell expansion by preventing cell turnover caused by physiological cell death mechanisms. In addition to its role in the development of human tumors, high levels of Bcl-2 expression are thought to play an important role in the resistance of tumor cells to cytotoxic anticancer drugs and radiation.

6. The mechanism by which Bcl-2 inhibits apoptosis is still poorly understood.

Several potential mechanisms of action have been proposed for Bcl-2, including protection against oxidative stress (Hockenbery et al., 1993; Kane et al., 1993), regulation of intracellular $Ca^{2+}$ homeostasis (Lam, et al., 1993), antagonism of cell death proteases (e.g. ICE-like family of cysteine proteases) (Miura, et al., 1993) and other cell death effectors (e.g. bax) (Yin, et al., 1994), and association with the signal transducing proteins, R-ras and Faf-1 (Fernandez-Sarbia and Bischoff, 1993; Wang, et al., 1994). In addition, two recent reports have suggested that Bcl-2 may exert anti-apoptotic effects by delaying cell cycle progression (Mazel, et al., 1996; Borner, 1996). Despite these numerous proposed mechanisms, there is considerable contradictory evidence and no universal agreement in the cell death field as to how Bcl-2 actually works. Further elucidation of the precise mechanism(s) of action of Bcl-2 is a high research priority in the field.

7. No functional links have been identified between inhibitors of apoptosis and inhibitors of cell cycle.

According to the concept that the cell cycle is linked to apoptosis, one would predict that cellular genes that inhibit apoptosis would be functionally linked to genes that exert effects on the cell cycle. Along these lines, Bcl-2 has been shown to delay cell cycle progression (as stated above), and Bcl-2 has also been postulated to function as a nuclear "gatekeeper" that regulates nuclear access of cyclin-dependent kinases. However, to date, Bcl-2 has not been shown to directly interact with any proteins that affect the cell cycle.

8. Further investigation of the mechanism(s) underlaying the death repressor activity of Bcl-2, including the characterization of novel Bcl-2 interacting proteins, will provide new insights into apoptosis and diseases in which apoptosis plays a pathogenetic role.

Understanding how Bcl-2 inhibits cell death is a critical question that has important implications for an understanding of all physiologic processes that involve cell death.

B. Molecular Pathogenesis of Breast and Ovarian Cancer

1. Several genes are responsible for inherited breast and ovarian cancer.

The existence of one gene predisposing to breast and ovarian cancer on chromosome 17q21, BRCA1, was proven by linkage analysis several years ago (Hall, et al., 1990), and isolated in 1994 by positional cloning (Miki, et al., 1994; Futreal, et al., 1994). BRCA1 is mutated in the germline and the normal allele is lost in tumor tissue from approximately 50% of cases of hereditary breast and ovarian cancer (reviewed in Szabo and King, 1996). BRCA2, a second breast cancer susceptibility gene, has been mapped to chromosome 13q21 and is presently implicated in 20% of hereditary cases (reviewed in Szabo and King, 1996). At least two other genes, p53 and the androgen receptor are also responsible for inherited predisposition to breast cancer in families. Other epidemiologic studies have suggested that carriers of mutations in the ataxia telangieclasia gene and HRAS1 minisatellite locus are also at increased risk of breast cancer.

2. Molecular genetic evidence suggests chromosome 17q21 may contain a second tumor suppressor tumor suppressor gene (in addition to BRCA1) that is important in sporadic breast and ovarian cancer.

Allelic deletions of chromosome 17q21 (loss of heterozygosity [LOH] that include that BRCA1 region are found to occur in 50–70% of breast carcinomas (Futreal, et al., 1992; Cropp, et al., 1993; Saito, et al., 1993) and in up to 75% of ovarian carcinomas (Russell, et al., 1991; Sato, et al., 1991; Eccles, et al., 1991; Yang-Feng, et al., 1993). However, while several studies have confirmed the role of germline BRCA1 mutations in hereditary breast and ovarian cancers (Miki, et al., 1994; Futreal, et al., 1994), somatic mutations in BRCA1 have been found in very few cases of sporadic cancers (Futreal, et al., 1994; Takahashi, et al., 1995; Merajver, et al., 1995; Hosking, et al. 1995). This raises the strong possibility that the frequent allelic loss on chromosome 17q21 in sporadic breast and ovarian cancer reflects the involvement of an additional tumor suppressor gene. In further support of this hypothesis, more detailed deletion mapping of sporadic epithelial ovarian carcinomas has revealed a common deletion unit, located on chromosome 17q21 that is located approximately 60 kb centromeric to BRCA1 (Tangir, et al., 1996). Thus, the presence of LOH is sporadic ovarian cancer cases of a region of chromosome 17q21 that does not encompass BRCA1 may reflect the presence of an additional tumor suppressor gene.

SUMMARY OF THE INVENTION

This invention provides for an isolated nucleic acid which encodes a wildtype human Beclin. This invention also provides for a mutant human Beclin.

This invention also provides for a vector comprising the isolated nucleic acid which encodes a wildtype human Beclin operatively linked to a promoter of RNA transcription, specifically, the plasmid pSG5/beclin.

This invention also provides a method of obtaining a polypeptide in purified form, specifically a wildtype human Beclin. This invention also provides for purified wildtype human Beclin.

This invention also provides for an oligonucleotide of at least 15 nucleotides capable of specifically hybridizing with a unique sequence of nucleotides within a nucleic acid which encodes a wildtype Beclin without hybridizing to any sequence of nucleotides within a nucleic acid which encodes a mutant human Beclin. This invention also provides for an oligonucleotide of at least 15 nucleotides capable of specifically hybridizing with a unique sequence of nucleotides within a nucleic acid which encodes a mutant Beclin without hybridizing to any sequence of nucleotides within a nucleic acid which encodes a wildtype human Beclin.

This invention also provides for a method for detecting a mutant human Beclin in a subject. This invention also provides for a method for determining whether a subject has a predisposition for cancer. Further, this invention also provides a method for determining whether a subject has cancer.

This invention also provides a method for inhibiting cell proliferation in cells unable to regulate themselves.

This invention also provides a pharmaceutical composition comprising a wildtype human Beclin and a pharmaceutically acceptable carrier.

This invention also provides for a method for treating a subject who has cancer.

This invention also provides for a method for detecting the presence of human chromosomal region 17q21 in a sample of genomic DNA.

This invention also provides for a method for treating a subject unable to control apoptosis in the cells of the subject.

BRIEF DESCRIPTION OF THE FIGURES

FIGS. 1A and 1B. Deduced amino acid sequence and nucleotide sequence of human beclin.

FIG. 1A. The deduced amino acid sequence (Seq. I.D. No.: 1) was used to scan various data banks. The boxed area represents the Bcl-2 binding domain of human Beclin (see Table 1) and the underlined area corresponds to the region that is predicted to have a coiled-coil conformation.

FIG. 1B. The nucleotide sequence of human Beclin (Sequence I.D. No.: 2). The partial nucleotide sequence of mouse Beclin obtained from sequencing clone F1 was aligned with an overlapping clone GT197 isolated from human fibroblasts (Rommens, 1995) and used to design primers to amplify the human beclin coding sequence from a normalized human brain infant cDNA library.

FIG. 2A. Western blot analysis of cell lysates prepared from BHK cells infected with a recombinant Sindbis virus chimera containing a flag epitope tagged human beclin insert (lane 2) or a control recombinant Sindbis virus chimera (lane 1) and probed with an anti-flag antibody (M2).

FIG. 2B. Northern blot analysis of beclin mRNA expression in human and mouse tissues. Human and mouse multiple tissue blots (Clontech) were hybridized with $^{32}$P-labeled human or mouse beclin probes (nucleotides 1–485), respectively, according to manufacturer's instructions. Beclin-specific probes hybridized to 2.3 kb transcripts in all tissues examined.

FIG. 2C. Immunofluorescence staining of human bcl-2 in a BHK cell.

FIG. 2D. Immunofluorescence staining of human beclin in the same BHK cell shown in FIG. 2C.

FIG. 3A. Cell viability of BHK cell death after infection with recombinant Sindbis viruses containing bcl-2 in either the sense (SIN/bcl-2) or antisense orientation (SIN/antisense bcl-2) or beclin in either the sense (SIN/beclin) or antisense orientation (SIN/antisense beclin).

FIG. 3B. Cell viability of AT3/Bcl-2 cells after infection with SIN/CAT, SIN/beclin, SIN/antisense beclin, or SIN/antisense bcl-2.

FIG. 4A. Determination of total cell number.

FIG. 4B. Determination of percentage of cell viability.

DETAILED DESCRIPTION OF THE INVENTION

Figure 2A:
FIGS. 2A, 2B, 2C and 2D. Beclin mRNA and protein expression. For FIGS. 2C and 2D, cells were co-transfected with 4 μg of pSG5/human bcl-2 and 4 μg of pSG5/beclin using lipofectin and fixed after 48 hours with 100% ETOH. Beclin expression was detected with a monoclonal anti-flag M2 Ab (1:20) and FITC-conjugated horse anti-mouse IgG Ab and Bcl-2 expression was detected with a polyclonal rabbit anti-Bcl-2 Ab and rhodamine-conjugated goat anti-rabbit Ab. Individual co-transfected cells were analyzed with confocal laser microscopy.

In order to facilitate an understanding of the Experimental Details section which follows, certain frequently occurring methods and/or terms are best described in Sambrook, et al.(1989).

Throughout this application, references to specific nucleotides are to nucleotides present on the coding strand of the nucleic acid. The following standard abbreviations are used throughout the specification to indicate specific nucleotides:

| C = cytosine | A = adenosine |
|---|---|
| T = thymidine | G = guanosine |

A "gene" means a nucleic acid molecule, the sequence of which includes all the information required for the normal regulated production of a particular protein, including the structural coding sequence, promoters and enhancers.

As used herein a wildtype human Beclin means a polypeptide which has an amino acid sequence identical to that present in a naturally-occurring form of human Beclin. As used here a mutant human Beclin means a polypeptide having an amino acid sequence which differs by one or more amino residues from, any naturally occurring form, including deletions mutants containing less than all of the residues present in the wildtype polypeptide, substitution homologs wherein one or more residues are replaced by other residues, and addition homologs wherein on or more amino acid residues are added to a terminal or medial portion of the polypeptide.

The nucleic acids and oligonucleotides described and claimed herein are useful for the information which they claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

The present invention provides for an isolated nucleic acid which encodes a wildtype human Beclin. This invention further provides an isolated nucleic acid which encodes a mutant human Beclin. The above-described isolated nucleic acids can be DNA, specifically cDNA or genomic DNA, and RNA. In a preferred embodiment, the wildtype Beclin has an amino acid sequence substantially identical to the amino acid sequence designated Seq. I.D. No.: 1. In another preferred embodiment, the isolated nucleic acid comprises a nucleic acid having a sequence substantially the same as the sequence designated Seq. I.D. No.: 2.

As used herein, "mutant human Beclin" means polypeptides whose nucleic acid sequence or amino acid seqeunce differs from that of the naturally-occuring wildtype human Beclin. For example, due to a point mutation, the translated polypeptide differs from the naturally-occuring wildtype protein. Further, a subject may have low expression of the naturally-occurring protein so that the cells with this low-expressing protein cannot inhibit cell proliferation.

This invention also provides for a vector comprising the above-described nucleic acid operatively linked to a promoter of RNA transcription.

Numerous vector backbones are known in the art and are useful for expressing proteins. Such vectors include plasmid vectors, cosmid vectors, yeast artificial chromosome (YAC), bacteriophage or eukaryotic viral DNA. For example, one such class of vectors comprises DNA elements derived from viruses such as bovine papilloma virus, polyoma virus, adenovirus, vaccinia virus, baculovirus, retroviruses (RSV, MMTV or MoMLV), Semliki Forest virus or SV40 virus.

Such vectors may be obtained commercially or assembled from the sequences described by methods well-known in the art.

Figure 5:
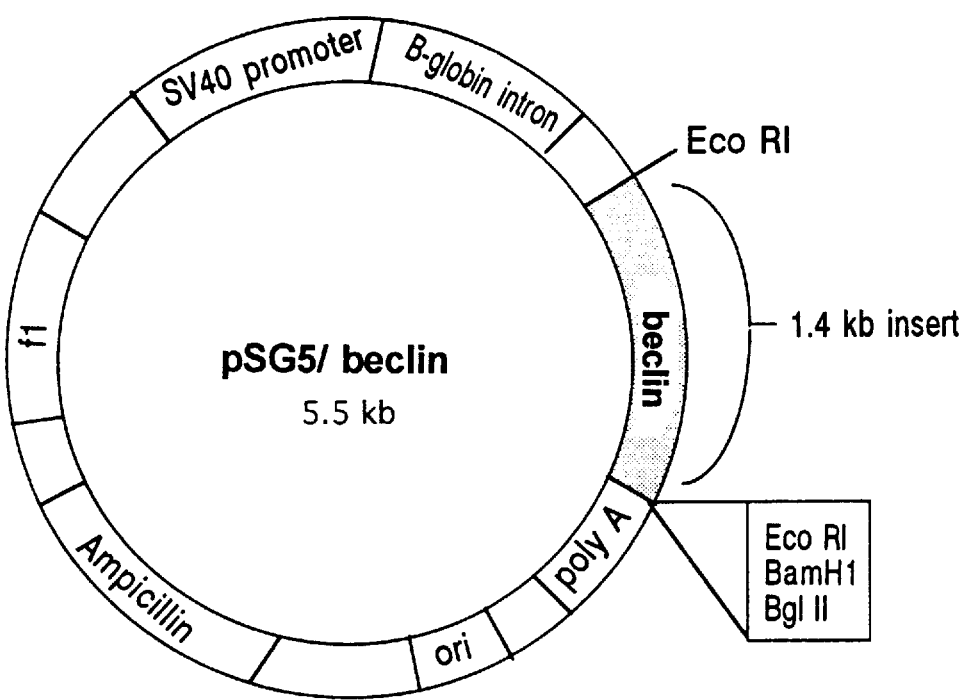
FIG. 5. Diagram of plasmid pSG5/beclin (ATCC Accession No. 97664). The 1.4 kb insert encoding Beclin was inserted into Eco RI sites in the plasmid, pSG5 (Stratagene).

This invention specifically provides a plasmid designated pSG5/beclin. Plasmid pSG5/beclin was made by cleaving DNA which encodes a wildtype human Beclin and inserting the DNA into the Eco RI site of pSG5 (FIG. 5). pSG5/beclin was deposited on Jul. 18, 1996 with the American Type Culture Collection (ATCC), 12301 Parklawn Drive, Rockville, Md. 20852, U.S.A., under the provisions of the Budapest Treaty For The International Recognition Of The Deposit Of Microorganisms For The Purposes Of Patent Procedure. pSG5/beclin has been accorded ATCC Accession Number 97664.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk$^-$ cells and COS cells. Mammalian cells may be transfected by methods well known in the art such as calcium phosphate precipitation, electroporation and microinjection.

This invention also provides a host vector system for the production of a polypeptide which comprises the above-described vector in a suitable host.

This invention also provides a method of producing a polypeptide which comprises growing the above-described host vector system, under suitable conditions permitting production of the polypeptide and recovering the polypeptide so produced. Further, this invention also provides a method of obtaining a polypeptide in purified form which comprises (a) introducing the above-described vector into a suitable host cell, (b) culturing the resulting host cell so as to produce the polypeptide, (c) recovering the polypeptide produced into step (b); and (d) purifying the polypeptide so recovered. In the above-described method, the vector comprises a plasmid, cosmid, yeast artificial chromosome (YAC), bacteriophage or eukaryotic viral DNA and the suitable host cell comprises a bacterial, insect, plant or mammalian cell.

This invention also provides a purified, wildtype human Beclin. Wildtype human Beclin means a polypeptide which has an amino acid sequence identical to that present in a naturally-occurring form of human Beclin.

This invention also provides an oligonucleotide of at least 15 nucleotides capable of specifically hybridizing with a unique sequence of nucleotides within a nucleic acid which encodes a wildtype Beclin without hybridizing to any sequence of nucleotides within a nucleic acid which encodes a mutant human Beclin. Further, this invention also provides an oligonucleotide of at least 15 nucleotides capable of specifically hybridizing with a unique sequence of nucleotides within a nucleic acid which encodes a mutant Beclin without hybridizing to any sequence of nucleotides within a nucleic acid which encodes a wildtype human Beclin. The above-described oligonucleotides may DNA or RNA. Methods of manufacturing such oligonucleotides and using the oligonucleotides are well-known in the art.

This invention also provides a method for determining whether a subject has a predisposition for cancer which comprises (a) obtaining an appropriate nucleic acid sample from the subject; and (b) determining whether the nucleic acid sample from step (a) is, or is derived from, a nucleic acid which encodes a mutant human Beclin so as to thereby determine whether a subject has a predisposition for cancer. Various methods of determining whether the nucleic acid sample is, or is derived from, a nucleic acid which encodes a mutant human Beclin exist.

In one example, the nucleic acid sample in step (a) comprises mRNA corresponding to the transcript of DNA encoding a mutant Beclin, and wherein the determining of step (b) comprises (i) contacting the mRNA with the above-described oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting binding of the mRNA to the oligonucleotide so as to form a complex, (ii) isolating the complex so formed, and (iii) identifying the MRNA in the isolated complex so as to thereby determine whether the MRNA is, or is derived from, a nucleic acid which encodes a mutant human Beclin.

In another example, the determining of step (b) comprises (i) contacting the nucleic acid sample of step (a), and the isolated nucleic acid which encodes a wildtype human Beclin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes a mutant human Beclin.

In another example, the determining of step (b) comprises (i) sequencing the nucleic acid sample of step (a); and (ii) comparing the nucleic acid sequence of step (i) with the above-described isolated nucleic acid having a sequence substantially the same as the sequence designated Seq. I.D. No.: 2, so as to thereby determine whether the nucleic acid sample is, or is derived from, a nucleic acid which encodes a mutant human Beclin.

In another example, the nucleic acid sample in step (a) comprises mRNA corresponding to the transcript of DNA encoding mutant Beclin, and wherein the determining of step (b) comprises (i) translating the mRNA under suitable conditions to obtain an amino acid sequence; and (ii) comparing the amino acid sequence of step (i) with the above-described isolated nucleic acid which as an amino acid sequence designated Seq. I.D. No.: 1 so as to thereby determine whether the nucleic acid sample is, or is derived from, a nucleic acid which encodes a mutant human Beclin.

In another example, the determining of step (b) comprises (i) amplifying the nucleic acid present in the sample of step (a); and (ii) detecting the presence of the mutant human Beclin in the resulting amplified nucleic acid.

The above-described methods of determining are well-known to those skilled in the art. In a preferred embodiment, the isolated nucleic acid or the oligonucleotide is labeled with a detectable marker, wherein the detectable marker is a radioactive isotope, a fluorophor or an enzyme.

Further, in a specific embodiment, the sample comprises blood, tissue or sera.

This invention also provides a method for determining whether a subject has cancer, which comprises (a) obtaining an appropriate nucleic acid sample from the subject; and (b)

determining whether the nucleic acid sample from step (a) is, or is derived from, a nucleic acid which encodes a mutant human Beclin so as to thereby determine whether a subject has cancer.

Various methods of determining whether the nucleic acid sample is, or is derived from, a nucleic acid which encodes a mutant human Beclin exist.

In one example, the nucleic acid sample in step (a) comprises mRNA corresponding to the transcript of DNA encoding a mutant Beclin, and wherein the determining of step (b) comprises (i) contacting the mRNA with the above-described oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting binding of the mRNA to the oligonucleotide so as to form a complex, (ii) isolating the complex so formed, and (iii) identifying the mRNA in the isolated complex so as to thereby determine whether the mRNA is, or is derived from, a nucleic acid which encodes a mutant human Beclin.

In another example, the determining of step (b) comprises (i) contacting the nucleic acid sample of step (a), and the isolated nucleic acid which encodes a wildtype human Beclin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes a mutant human Beclin.

In another example, the determining of step (b) comprises (i) sequencing the nucleic acid sample of step (a); and (ii) comparing the nucleic acid sequence of step (i) with the above-described isolated nucleic acid having a sequence substantially the same as the sequence designated Seq. I.D. No.: 2, so as to thereby determine whether the nucleic acid sample is, or is derived from, a nucleic acid which encodes a mutant human Beclin.

In another example, the nucleic acid sample in step (a) comprises mRNA corresponding to the transcript of DNA encoding mutant Beclin, and wherein the determining of step (b) comprises (i) translating the mRNA under suitable conditions to obtain an amino acid sequence; and (ii) comparing the amino acid sequence of step (i) with the above-described isolated nucleic acid which as an amino acid sequence designated Seq. I.D. No.: 1 so as to thereby determine whether the nucleic acid sample is, or is derived from, a nucleic acid which encodes a mutant human Beclin.

In another example, the determining of step (b) comprises (i) amplifying the nucleic acid present in the sample of step (a), and (ii) detecting the presence of the mutant human Beclin in the resulting amplified nucleic acid.

The above-described methods of determining are well-known to those skilled in the art. In a preferred embodiment, the isolated nucleic acid or the oligonucleotide is labeled with a detectable marker, wherein the detectable marker is a radioactive isotope, a fluorophor or an enzyme.

Further, in a specific embodiment, the sample comprises blood, tissue or sera.

This invention also provides for a method for inhibiting cell proliferation in cells unable to regulate themselves by introducing the isolated nucleic acid which encodes a wildtype human Beclin into the cells, specifically wherein the cells are cancerous. Various methods of introducing nucleic acids into cells are well-known to those skilled in the art.

This invention also provides a method for treating a subject who has cancer which comprises introducing the isolated nucleic acid which encodes a wildtype human Beclin, into the subject so as to thereby treat the cancer. Various methods of introducing nucleic acids into cells are well-kwown to those skilled in the art. In one example, one can introduce the isolated nucleic acid by (a) recovering cancer cells from the subject, (b) introducing the isolated nucleic acid of claim 1 into the cells; and (c) reintroducing the cells of step (b) into the subject so as to treat the subject who has cancer. Many types of cancer cells exist and are well-known in the art, specifically, breast, ovarian, skeletal, cervical, colon, prostate or lung cells.

This invention also provides a pharmaceutical composition comprising a purified wildtype human Beclin and a pharmaceutically acceptable carrier. This invention further provides a pharmaceutical composition comprising the polypeptide obtained from using the above-described method of obtaining a polypeptide in a purified form and a pharmaceutically acceptable carrier.

This invention also provides a method for treating a subject who has cancer comprising administration of an effective amount of the above-described pharmaceutical compositions to the subject who has cancer. The administration of the pharmaceutical compositions may be by topical, oral, aerosol, subcutaneous administration, infusion, intralesional, intramuscular, intraperitoneal, intratumoral, intratracheal, intravenous injection, or liposome-mediate delivery.

This invention also provides a method for detecting the presence of human chromosomal region 17q21 in a sample of genomic DNA which comprises (a) contacting the sample with the isolated nucleic acid which encodes a wildtype human Beclin, under conditions permitting formation of a complex between any genomic DNA present in the sample that is complementary to such nucleic acid, and (b) detecting the presence of any complex formed in step (a), the presence of such a complex indicating the human chromosomal region 17q21 is present in the sample. Further, one may contacting the sample with an oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting formation of a complex between any genomic DNA present in the sample that is complementary to such oligonucleotide, and (b) detecting the presence of any complex formed in step (a), the presence of such a complex indicating the human chromosomal region 17q21 is present in the sample. The nucleic acid may be labeled with a detectable marker, wherein the detectable marker is a radioactive isotope, a fluophor or an enzyme.

This invention also provides a method for detecting a mutant human Beclin in a subject which comprises (a) obtaining an appropriate nucleic acid sample from the subject, and (b) determining whether the nucleic acid sample from step (a) is, or is derived from, a nucleic acid which encodes mutant human Beclin so as to thereby detect a mutant human Beclin in the subject.

Various methods of determining whether the nucleic acid sample is, or is derived from, a nucleic acid which encodes a mutant human Beclin exist.

In one example, the nucleic acid sample in step (a) comprises mRNA corresponding to the transcript of DNA encoding a mutant Beclin, and wherein the determining of step (b) comprises (i) contacting the mRNA with the above-described oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting binding of the mRNA to the oligonucleotide so as to form a complex, (ii) isolating the complex so formed, and (iii) identifying the mRNA in the isolated complex so as to thereby determine whether the mRNA is, or is derived from, a nucleic acid which encodes a mutant human Beclin.

In another example, the determining of step (b) comprises (i) contacting the nucleic acid sample of step (a), and the isolated nucleic acid which encodes a wildtype human Beclin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes a mutant human Beclin.

In another example, the determining of step (b) comprises (i) sequencing the nucleic acid sample of step (a); and (ii) comparing the nucleic acid sequence of step (i) with the above-described isolated nucleic acid having a sequence substantially the same as the sequence designated Seq. I.D. No,: 2, so as to thereby determine whether the nucleic acid sample is, or is derived from, a nucleic acid which encodes a mutant human Beclin.

In another example, the nucleic acid sample in step (a) comprises mRNA corresponding to the transcript of DNA encoding mutant Beclin, and wherein the determining of step (b) comprises (i) translating the mRNA under suitable conditions to obtain an amino acid sequence; and (ii) comparing the amino acid sequence of step (i) with the above-described isolated nucleic acid which as an amino acid sequence designated Seq. I.D. No.: 1 so as to thereby determine whether the nucleic acid sample is, or is derived from, a nucleic acid which encodes a mutant human Beclin.

In another example, the determining of step (b) comprises (i) amplifying the nucleic acid present in the sample of step (a); and (ii) detecting the presence of the mutant human Beclin in the resulting amplified nucleic acid.

The above-described methods of determining are well-known to those skilled in the art. In a preferred embodiment, the isolated nucleic acid or the oligonucleotide is labeled with a detectable marker, wherein the detectable marker is a radioactive isotope, a fluorophor or an enzyme.

Further, in a specific embodiment, the sample comprises blood, tissue or sera.

This invention also provides a method for treating a subject unable to control apoptosis in the cells of the subject which comprises introducing the isolated nucleic acid of claim 1, into the subject so as to treat the subject unable to control apoptosis in the cells of the subject. In a specific embodiment, the cells are cancerous. Various method of introducing isolated nucleic acids into cells exist and are well-known in the art. In one example, one can introduce the isolated nucleic acid by (a) recovering cancer cells from the subject, (b) introducing the isolated nucleic acid of claim 1 into the cells; and (c) reintroducing the cells of step (b) into the subject so as to treat the subject who has cancer.

This invention also provides a method of treating a subject unable to control apoptosis in the cells of the subject comprising administration of an effective amount of the above-described pharmaceutical compositions to the subject, wherein the administration comprises, topical, oral, aerosol, subcutaneous administration, infusion, intralesional, intramuscular, intraperitoneal, intratumoral, intratracheal, intravenous injection, or liposome-mediate delivery.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Cell proliferation and apoptosis may share common pathways. Yet no functional links have been identified between cellular genes that inhibit apoptosis and cellular genes that inhibit proliferation. To investigate the mechanism by which anti-apoptotic genes function, the yeast two hybrid system was used to screen an adult mouse brain cDNA library for genes encoding proteins that interact with Bcl-2. Both Bcl-2 and its related family member, Bcl-$x_L$, interact with a novel 60 kd protein, Beclin, encoded by a gene on a specific region of chromosome 17q21 that is postulated to contain a tumor suppressor gene important in sporadic breast and ovarian cancer. Mutations in the conserved BH1 domains of Bcl-2 and Bcl-$x_L$ that block anti-apoptotic function also disrupt binding with Beclin, suggesting that Bcl-2-Beclin and Bcl-$x_L$-Beclin interactions may be important for inhibition of apoptosis. Using Sindbis virus as a vector and inducer of apoptosis in mammalian cells, antisense beclin RNA partially blocks the death-repressor activity of Bcl-2 and overexpression of Beclin induces a proliferative arrest. Thus, Bcl-2 may inhibit apoptosis by interacting with a gene that has effects on cellular proliferative machinery.

The common deletion unit, located approximately 60 kb centromeric to BRCA1 that is postulated to contain an additional tumor suppressor gene important for ovarian and possibly breast cancer, contains 12 previously identified genes (Friedman, et al., 1995). Six of them are known genes or human homologs of other species, gamma tubulin, homolog of D. melanogaster enhancer of zeste, pseudogene of HMG17, homolog of Pacific electric ray VAT1, glucose-6phosphatase and Ki antigen. The remaining six genes are novel genes, one of which is the gene referred to as beclin that is described in this invention.

The mapping of beclin to this common deletion unit on chromosome 17q21, coupled with data that Beclin interacts with Bcl-2 and has anti-proliferative effects, raises the possibility that Beclin may function as a tumor suppressor gene important in ovarian and breast cancer.

EXAMPLE 1

Yeast Two Hybrid CDNA Library Screen To Isolate Bcl-2-interacting Proteins

To further understand the mechanism by which bcl-2 protects against apoptosis, the yeast two hybrid system was used to screen a mouse brain library for complementary cDNAs encoding proteins that bind to Bcl-2. A bait plasmid (pGBT9/bcl-2) was constructed by fusing human bcl-2 (lacking the C' terminal signal-anchor sequence to ensure translocation to the nucleus) to the GAL4 DNA-binding domain, which was cotransformed with an oligo(dT) and random hexamer primed adult mouse brain cDNA fusion library in a GAL4-activating domain vector, pGAD10.

pGBT9/bcl-2 was co-transformed with 1×10⁶ cDNAs from a mouse brain library fused to a GAL-4 activation domain vector (Clontech), plated onto SD medium lacking tryptophan and leucine, and after incubation at 30° C. for 4 days, screened for LacZ activity using a colony lift filter assay. Putative interacting clones were isolated by manipulation in leuB *E. coli,* and further tested against pGBT9 and control plasmids. Of one million transformants, one true positive colony (F1) was identified by the X-Gal filter assay. A positive β-gal reaction between pGBT9/bcl-2 and clone F1 was obtained within 15–20 minutes. The sequence of the Eco RI insert in clone F1 was obtained using Sequenase(™) and by automated dideoxy sequencing. Sequencing analysis of the cDNA plasmid rescued from this colony revealed a termination codon 42 base pairs downstream from the GAL 4 activation domain, several predicted short open reading frames between nucleotides 124 and 1843, and a longer predicted open reading frame spanning from nucleotide 1855 to the 3' end of the insert, suggesting that either the 14 amino acid fusion protein was interacting with Bcl-2, or one of the downstream open reading frames encoded a protein that contains its own activation domain and interacts with Bcl-2. To identify the Bcl-2-interacting region of F1, nucleotides 1–1854 and 1855–2500 were fused to the GAL4 activation domain in pGAD424 and tested for interactions with Bcl-2. Nucleotides 1855–2500, but not 1–1800, encoded a protein that specifically interacts with Bcl-2 (Table 1).

A database search revealed that the sequence of F1:1855–2500 overlapped with several clones isolated from a normalized infant human brain cDNA library in the Merck EST database as well as clones from human breast (GT197) (Rommens, 1995) and human fibroblast cells (B32) (Friedman, 1994). Clones GT197 and B32 were both isolated in the generation of transcription maps of the breast cancer susceptibility locus on chromosome 17q21 and are mapped to a region located approximately 100 kilobases centromeric to the gene BRCA1. These clones contain only partial open reading frames of a novel gene that encodes a protein with coiled coils. The gene was assigned the name beclin, because of the interaction of its encoded protein with bcl-2 (becl) and the predicted coiled coil structure of its encoded protein (in suffix). The overlapping partial clones in Genbank were aligned with the mouse beclin sequence to obtain a predicted sequence of the full-length open reading frame for human beclin. Human beclin was isolated from a normalized human brain infant cDNA library (Soares, 1994).

Additional yeast two hybrid studies were performed to confirm that human beclin, like mouse beclin, encodes a protein that interacts with human Bcl-2, and to further define the Bcl-2-interacting region of human Beclin (see Table 1). Additional clones containing fragments of F1 or human beclin fused to the GAL4-activiation domain were constructed using PCR primers which incorporated Eco Ri and Sal I restriction sites into the forward and reverse primers, respectively. The ability of human beclin to bind to Bcl-2 in the yeast two hybrid system maps to amino acids 88–150. Interestingly, the coding sequence for this region of Beclin is deleted in some human infant brain cDNA clones in the Merck EST database, suggesting that Beclin exists in at least two forms—one form that contains a Bcl-2 binding domain and one form that lacks a Bcl-2 binding domain.

Figure 1A:
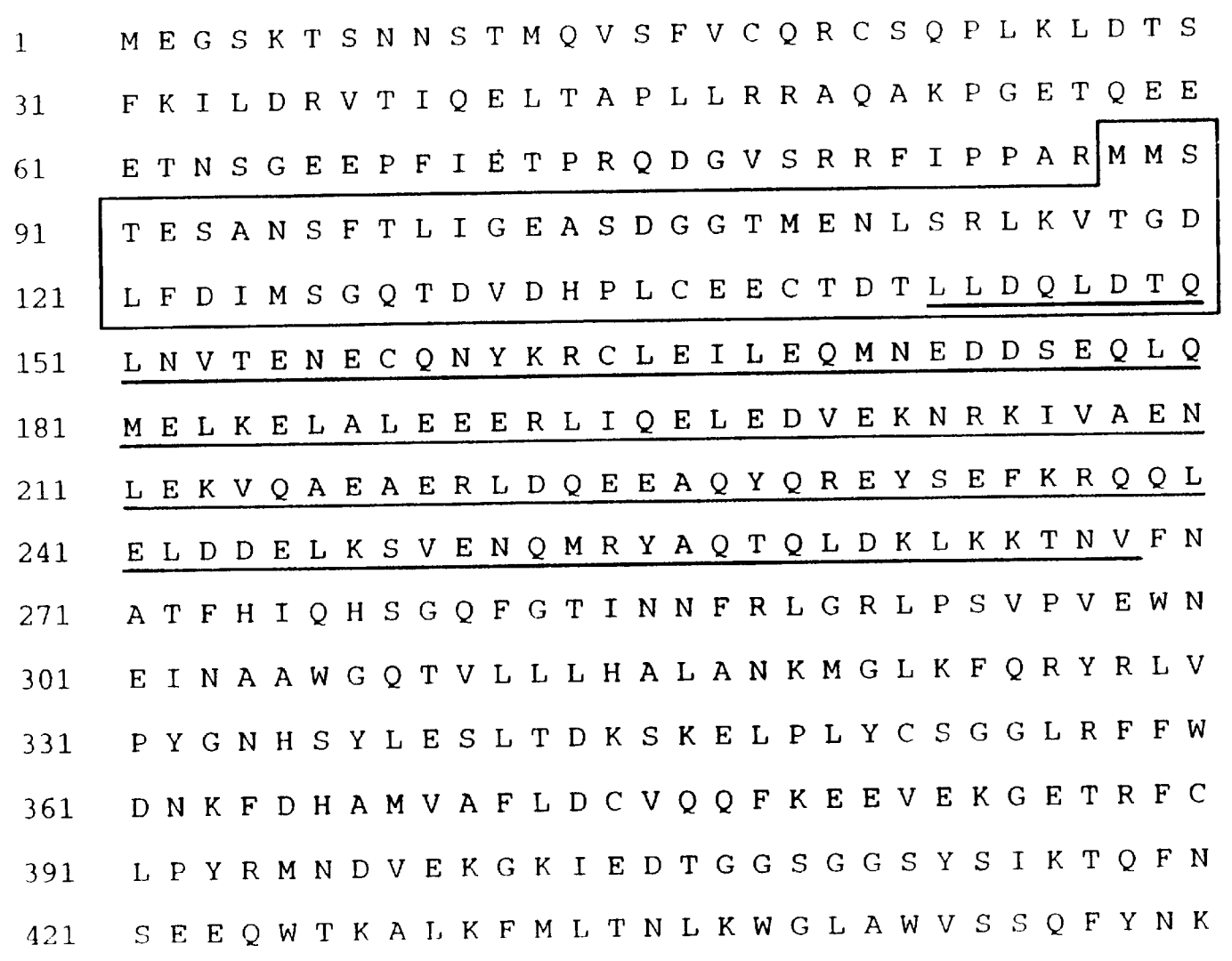

Sequencing Of Human Beclin. Primers immediately upstream and downstream of the predicted open reading frame were used to amplify the coding sequence of human beclin from a normalized human infant brain cDNA library (Soares, 1994). The resulting PCR products from several independent reactions were cloned into pCR$^{TMII}$ and sequenced in both directions using Sequenase (US Biochemicals) as well as automated sequencing. The resulting nucleotide sequence (FIG. 1B, Seq. I.D. No.: 2) and deduced amino acid sequence (FIG. 1A, Sequ. I.D. No.: 1) were used to scan various data banks (Genbank, EMBL, SwissProt, PIR) for homologous sequences using the BLAST algorithms (Altschul, 1990). The amino acid sequence was also analyzed by the PROSITE program to identify functional motifs and by the COILS program to identify coiled coil regions (Lupas, 1991).

Yeast Two Hybrid Analyses of Beclin-Bcl-2 Family Member Interactions. To investigate whether Beclin interacts with other Bcl-2 family members that positively or negatively regulate apoptosis, bax, bcl-$x_S$ and bcl-$x_L$ cDNAs were fused into the GAL4 binding domain vector and tested for interactions with Beclin in the yeast two hybrid system. (See Table 1).

The sequences encoding amino acids 1–218 of human bcl-2, 1–212 of bcl-$X_L$, 1–149 of bcl-$x_S$, and 1–171 of bax were cloned into pGBT9 in frame with the GAL4-binding domain. To avoid problems with targeting of proteins to the nucleus, the sequences encoding C'terminal transmembrane domains were omitted. To construct pGBT9/bcl-2, human bcl-2 was amplified by PCR from the plasmid pZIP/bcl-2, subcloned into pCR$^{TMII}$, and the correct sequence of bcl-2 was confirmed prior to cloning an Eco RI-Sal I fragment into pGBT9. To construct pGBT9/bcl-$x_L$, pGBT9/bcl-$x_S$, and

TABLE 1

Summary of yeast two-hybrid assay results

| | GAL4 BD | | | | | | |
|---|---|---|---|---|---|---|---|
| GAL4 AD | Empty | Bcl-2 | Bcl-$X_L$ | Bcl-$X_S$ | Bax | Lamin | p53 |
| Empty | — | — | — | + | — | — | — |
| F1 | — | + | + | ND | — | — | — |
| F1:1–1855 | — | — | — | ND | — | — | — |
| F1:1856–2563 (Mus Beclin 1–708) | — | + | + | ND | — | — | — |
| Hu Beclin 1–708 | — | + | + | ND | — | — | — |
| Hu Beclin 1–450 | — | + | + | ND | — | — | — |
| Hu Beclin 1–258 | — | — | — | ND | — | — | — |
| Hu Beclin 262–450 | — | + | + | ND | — | — | — |
| Hu Beclin 451–708 | — | — | — | ND | — | — | — |
| Hu Beclin 1–1383 | — | — | — | ND | — | — | — | pGBT6/Bax, the Eco RI—Xho I fragments were excised from pGEG202 plasmids previously described (Sato, et al., 1994) and cloned into the Eco RI—Sal I sites of pGBT9. Control pGBT9 plasmids containing lamin (pLAM5') and p53 (pVA3) inserts were obtained from Clontech.

The Bcl-$x_s$ GAL4 DB construct activated transcription by itself, and therefore could not be tested for interactions with Beclin. The same region of Beclin (aa 88–150) that interacted with Bcl-2, also interacted with Bcl-$x_L$ (Boise, 1993), a related Bcl-2 family member that inhibits apoptosis. In contrast, Beclin did not react with Bax (Oltvai, 1993), a family member that promotes apoptosis. The selective interaction of Beclin with Bcl-2 family members that have death repressor activity suggests a possible functional role of Beclin in anti-apoptotic pathways.

Full-length human Beclin does not interact with Bcl-2 in the yeast two-hybrid system. This most likely reflects lack of translocation to the nucleus in yeast secondary to association with yeast intracellular membranes since full-length human Beclin expressed in mammalian cells is associated with the insoluble membrane fraction after cell lysis.

To evaluate whether Bcl-2-Beclin and Bcl-$x_L$-Beclin interactions are related to the ability of Bcl-2 and Bcl-$X_L$ to inhibit apoptosis, pGBT9 vectors were constructed containing bcl-2 and bcl-$x_L$ constructs with mutations in the conserved BH1 domain that are known to block death repressor activity. A G→A mutation at amino acid position 145 of Bcl-2 completely abrogates Bcl-2 death-repressor activity in interleukin-3 deprivation, γ-irradiation and glucocorticoid-induced apoptosis (Yin, 1994), and also blocks Bcl-2 binding to beclin in the yeast two hybrid system (Table 2). Similarly, substitutions of amino acids 136–138 of Bcl-$x_L$ (VNW→AIL) completely abolishes death repressor activity in Sindbis virus-induced apoptosis (Cheng, 1996), and also blocks Bcl-$x_L$ binding to Beclin. Thus, mutations that block anti-death activity of bcl-2 and bcl-$x_L$ also block binding to beclin.

tagged Beclin confirms that human beclin encodes a 60 kd protein (FIG. 2A).

To construct the plasmid SIN/flag-beclin, human beclin was amplified by PCR from a human brain cDNA library, using primers that incorporated upstream and downstream Bst EII sites and an upstream sequence encoding the flag epitope. The Bst EII flag-beclin fragment was ligated into the Bst EII restriction site of the previously described double subgenomic SIN vector, ds633. Recombinant virus stocks were generated from SIN/flag-beclin plasmid as described. BHK cells were infected with SIN/flag-beclin or control constructs at a multiplicity of infection (MOI) of 1 plaque-forming unit per cell and harvested 15 hours after infection.

Figure 2B:
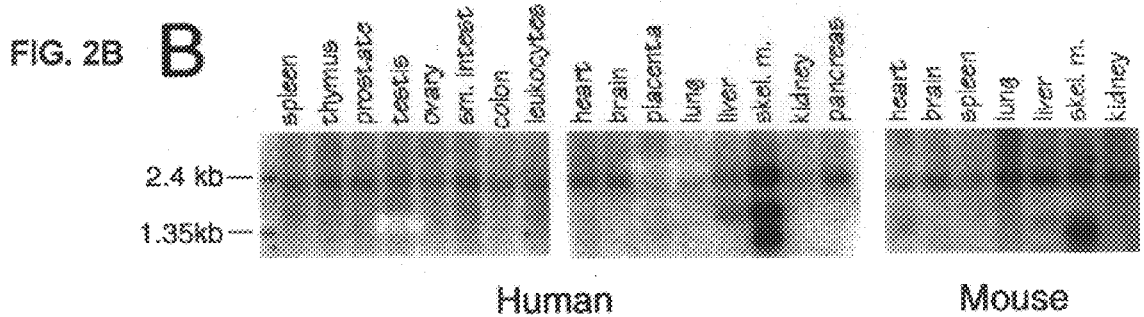

PROSITE analysis of human beclin identified several potential phosphorylation and myristoylation sites, but no other functional sequence motifs. RNA blot analysis revealed that expression of beclin mRNA is widespread in both mouse and human adult tissues. A beclin-specific probe hybridized to a 2.3 kb transcript present at highest levels in human skeletal muscle, but at detectable levels in all tissues examined (FIG. 2B). In some tissues, additional 1.7 and 1.4 kb transcripts were observed, suggesting the presence of alternatively spliced transcripts.

Multiple tissue Northern blots were probed according to manufacturer's instructions (Clontech) with a $^{32}$P-labeled 485 base pair probe corresponding to nucleotides 1–485 of human or mouse beclin. Equal amount of loading (2 μg of polyA) was confirmed by hybridization to a B-actin probe.

Figure 2C:
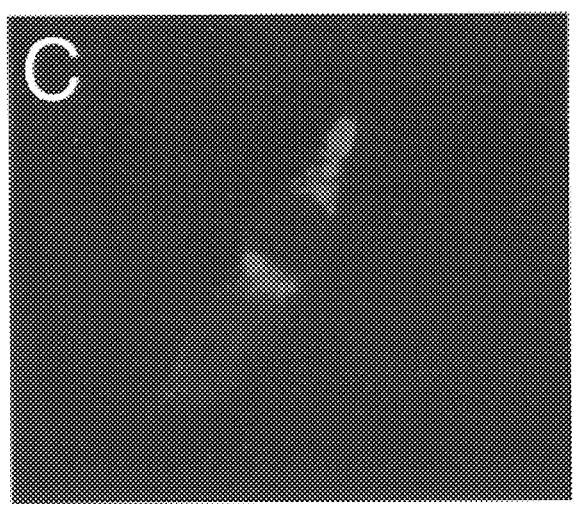
Figure 2D:
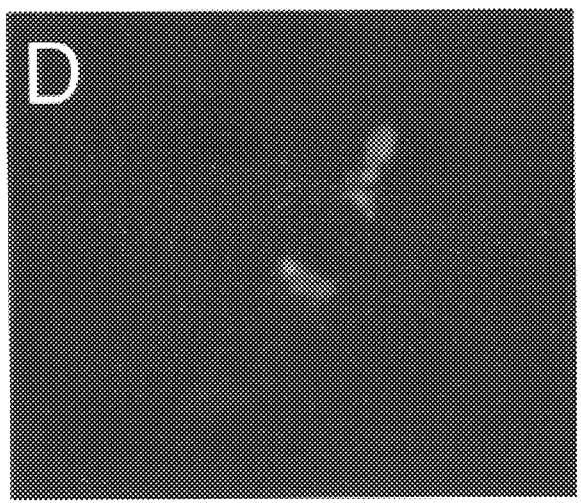

To examine the subcellular localization of Beclin in mammalian cells and to determine whether Beclin colocalizes with Bcl-2, baby hamster kidney cells were transmitted with the plasmids, pSG5/bcl-2 and pSG5/beclin, that express Bcl-2 and a flag-epitope tagged Beclin, respectively. Immunofluorescence staining with an anti-flag epitope antibody and an anti-Bcl-2 antibody revealed that both proteins were expressed in the perinuclear membrane/endoplasmic reticulum region (FIG. 2C). Confocal laser microscopy

TABLE 2

Effect of BH1 domain mutations on the ability of Bcl-2 and Bcl-$x_l$ to bind to beclin in the yeast two-hybrid assay

|  |  |  | Inhibition of Apoptosis | Beclin Binding |
| --- | --- | --- | --- | --- |
| WT BCL-2 | (SEQ. I.D. NO.: 3) | ELFRDGVNWGRIVAFFEFGG | + | + |
| WT BCL-$X_L$ | (SEQ. I.D. NO.: 4) | ELFRDGVNWGRIVAFFSFGG | + | + |
| MT BCL-2 | (SEQ. I.D. NO.: 5) | ---------A---------- | − | − |
| MT BCL-$X_L$ | (SEQ. I.D. NO.: 6) | ------AIL----------- | − | − |

Oligonucleotide-directed mutagenesis of bcl-2 and bcl-$x_L$ was accomplished by a two-step polymerase chain reaction. Mutants were cloned into pCR™11 and mutations were confirmed by dideoxy sequencing prior to cloning into pGBT9 pGBT9/bcl-2 and pGBT9/bcl-$x_L$ mutants were cotransformed with fragments of human beclin (1–450, 262–450, 1–708) fused to the GAL4-activation domain. Transformants wee screened by β-galactosidase assays to determine whether mutations affected Bcl-2 binding.

Analysis of Beclin Expression in Mammalian Cells

Human beclin is predicted to encode a novel 450 amino acid protein, containing a coiled coil region with 25–28% homology with myosin-like proteins (FIG. 1A). Western blot analysis of lysates prepared from BHK cells infected with a Sindbis virus vector that expresses flag epitope-confirmed an identical pattern of immunostaining for Bcl-2 and Beclin in all cotransfected cells. Thus, Bcl-2 and Beclin colocalize in transfected mammalian cells.

Role of Beclin in Virus-Induced Apoptosis

Figure 3A:
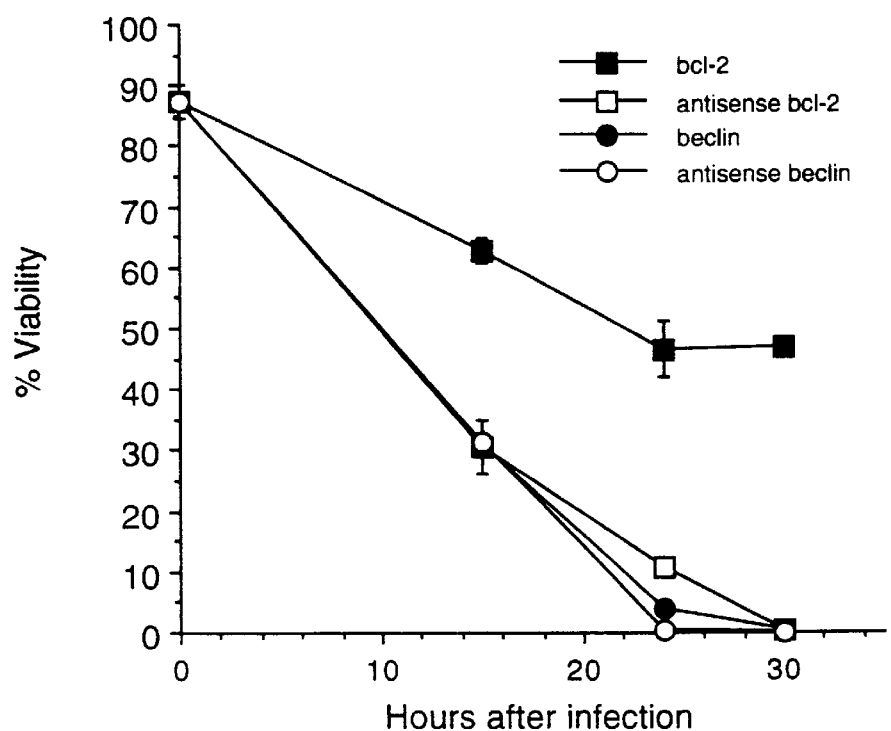
FIGS. 3A and 3B. Effect of beclin and antisense beclin on Sindbis virus-induced apoptosis. The recombinant chimeric viruses SIN/antisense bcl-2, SIN/antisense beclin were constructed using methods described for the construction of SIN/flag-beclin. Cell viability was determined by trypan blue exclusion. The results of triplicate wells are shown (mean=S.E.). Similar results were obtained in more than 5 independent experiments.

Overexpression of many Bcl-2 family members (Boise, 1993; Oltvai, 1993) or Bcl-2 interacting proteins (Farrow, Takayama) results in either the acceleration or inhibition of apoptosis. The Sindbis virus vector system was employed, which has been previously used to study the anti-apoptotic function of several Bcl-2 family members (Cheng, 1996), to evaluate the effects of beclin overexpression on virus-induced apoptosis. While Bcl-2 overexpression results in a significant delay in SIN-induced cell death of BHK cells (FIG. 3A), neither antisense beclin RNA nor beclin overexpression delays or accelerates virus-induced death.

Therefore, rather than acting as an independent regulator of apoptosis, beclin may be a functional component of a pathway that is mechanistically involved in the death repressor activity of Bcl-2.

Figure 3B:
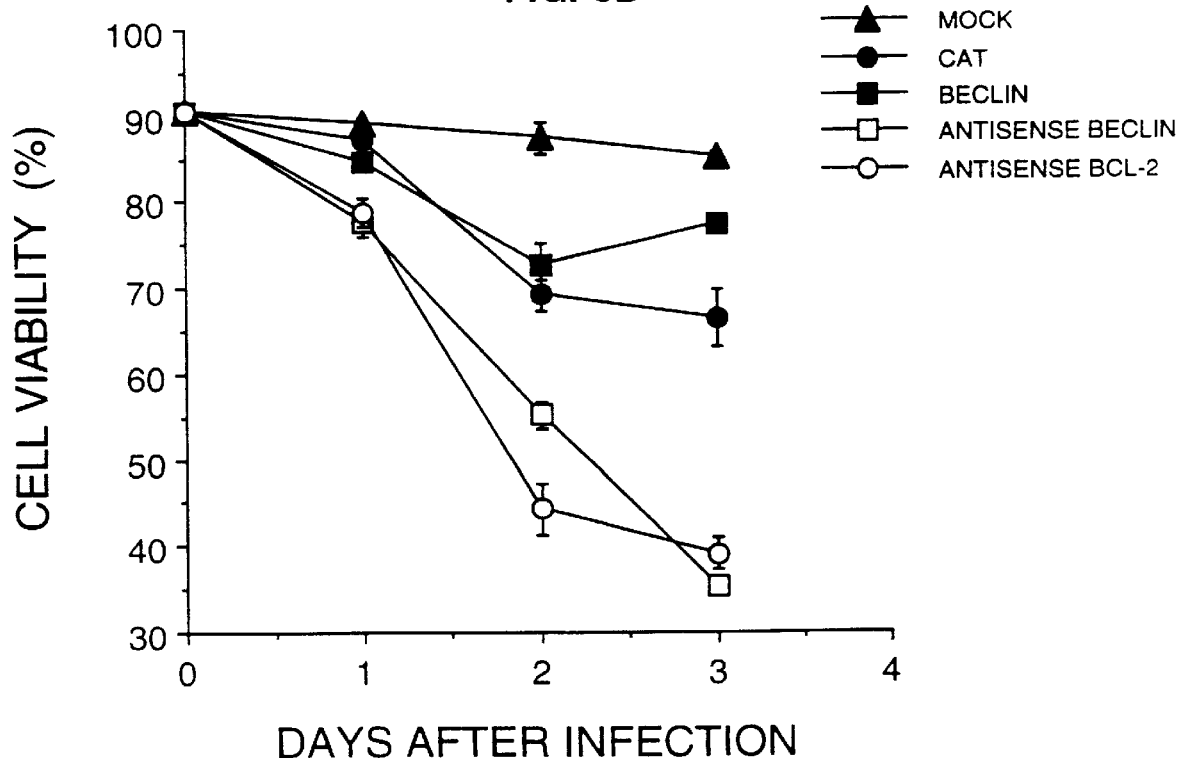

To test this hypothesis, Beclin was tested to see if it plays a role in the ability of Bcl-2 to inhibit virus-induced apoptosis in mammalian cells. A bcl-2-transfected rat prostate adenocarcinoma cell line (AT3/bcl-2 cells) that is resistant to Sindbis virus-induced apoptosis (Levine, 1996) was infected with chimeric Sindbis viruses containing beclin in either the sense or antisense orientation. At 72 hours after infection, 77% of cells infected with SIN/beclin and 66% of cells infected with a control chimeric virus, SIN/CAT were still alive (FIG. 3B). In contrast, only 35% of cells infected with SIN/antisense beclin were still alive. The magnitude of this increase in cell death is similar to that seen after infection with a virus containing bcl-2 antisense RNA. The ability of antisense beclin, like antisense bcl-2, to partially inhibit bcl-2 protection against Sindbis virus-induced apoptosis demonstrates a functional role for Beclin in the death repressor activity of Bcl-2.

Role of Beclin in Cellular Proliferation

Figure 4A:
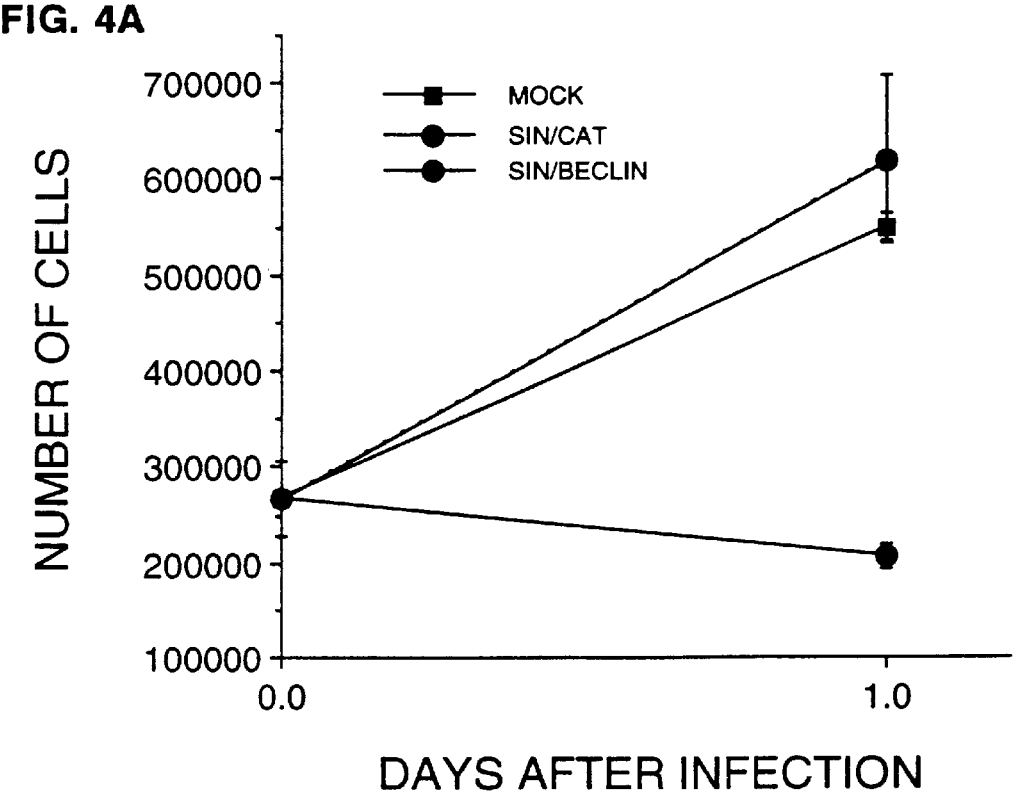
FIGS. 4A and 4B. Effect of beclin on AT3 cell proliferation. $5\times10^5$ cells were seeded in 35 mm wells and 24 hours later, infected with SIN/CAT, SIN/beclin, or mock-infected at a multiplicity of infection of 1 plaque-forming unit per cell. At the time of infection and 24 hours after infection, triplicate wells were stained with trypan blue and counted in a hemocytometer. Results are presented as means±s.e. Similar results were obtained in more than eight independent experiments.
Figure 4B:
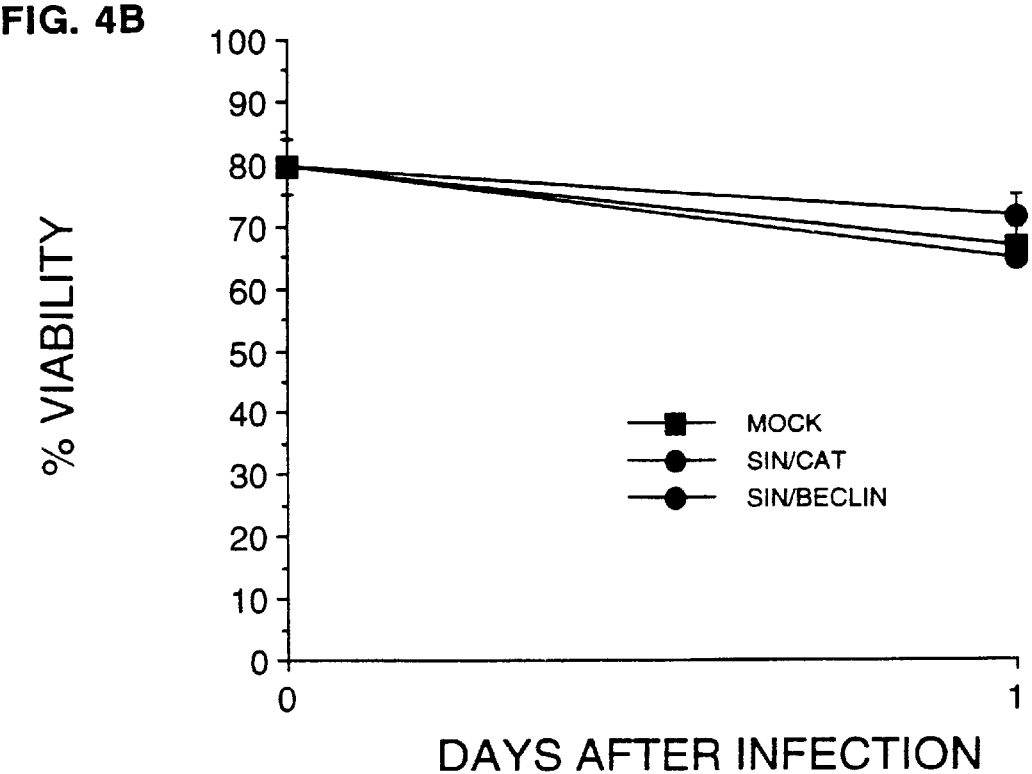

In the course of the above experiments, an apparent inhibition of cellular proliferation in both BHK cells and AT3/bcl-2 cells infected with SIN/beclin was observed. The number of AT3/bcl-2 cells 24 hours after infection with SIN/beclin was reduced by more than 50% as compared to the number of AT3/bcl-2 cells that were mock-infected or infected with SIN/CAT (FIG. 4A), whereas no significant differences were observed in AT3/bcl-2 cell viability among the three groups (FIG. 4B).

In summary, the yeast two hybrid system was used to isolate a cDNA that encodes a predicted coiled coil protein, Beclin, that interacts with members of the Bcl-2 family that negatively regulate apoptosis. A functional role for Beclin in anti-apoptotic pathways is suggested both by Bcl-2 and Bcl-$x_L$ mutational studies showing a correlation between disruption of anti-apoptotic function and binding to Beclin, and by studies in which beclin antisense RNA partially blocks Bcl-2-mediated protection against virus-induced apoptosis. While the function of beclin, when expressed at normal levels in mammalian cells, is still unknown, its overexpression can inhibit cellular proliferation. These observations are consistent with the hypothesis that Bcl-2 may inhibit apoptosis by interacting with a gene product that exerts effects on cellular proliferative machinery. Furthermore, these findings, coupled with previous studies that have mapped beclin transcripts to a breast and ovarian cancer susceptibility locus on chromosome 17q21 (Rommens, 1995; Friedman, 1994; Friedman, 1995), warrant additional investigation to determine whether beclin, and its interactions with Bcl-2, play a role in human cancer.

REFERENCES

1. Altschul, S. F., et al. (1990) "Basic local alignment search tool." *J. Mol. Biol.* 215: 403–410;

2. Boehme, S. A. and Lenardo, M. J. (1993) "Propriocidal apoptosis of mature T lymphomcytes occurs at S phase of the cell cycle." *Eur. J. Immunol* 23: 1552–1560;

3. Boise, L. H., et al. (1993) "Bcl-xL, a bcl-2-related gene that functions as a dominant regulator of apoptotic cell death." *Cell* 74: 597–608;

4. Borner, C. (1996) "Diminished cell proliferation associated with the death-protective activity of Bcl-2." *J. Biol. Chem.* 271: 12695–12698;

5. Boyd, J., et al. (1994) "Adenovirus E1B 19kDa and Bcl-2 proteins interact with a common set of cellular proteins."*Cell* 79: 341–351;

6. Buttyan, R. (1991) "Genetic response of prostate cells to androgen deprivation: insights into the cellular mechanisms of apoptosis." In Tomei L D, Cope F O (eds): *"Apoptosis: The Molecular Basis of Cell Death."* Plainview, N.Y.: Cold Spring Harbor Laboratory Press 157–173;

7. Cheng, E. H., et al. (1996) "Bax-independent inhibition of apoptosis by Bcl-$x_L$." *Nature* 379: 554–556.

8. Clarke, A., et al. (1992) "Requirement for a functional Rb-1 gene in murine development." *Nature* 359: 328–330

9. Chittenden, T. (1995) "Induction of apoptosis by the Bcl-2 homologue Bak." *Nature* 374: 733–736;

10. Cropp, C. S, et al. (1993) "Identification of three regions on chromosome 17q in primary human breast carcinomas which are frequently deleted." *Cancer Res.* 53: 3382–3385;

11. Eccles, D. M., et al. (1992) "Early loss heterozygosity on 17q in ovarian cancer." *Oncogene* 7: 2069–2072;

12. Evan, G. I., et al. (1995) "Apoptosis and the cell cycle." *Curr. Opin. Cell Biol.* 7: 825–834;

13. Evan, G. I., et al. (1996) "Induction of apoptosis in fibroblasts by c-myc protein." *Cell* 69: 119–128;

14. Evan, G. I., et al. (1995) "Apoptosis and the cell cycle." *Curr. Opin. Cell Biol.* 7: 825–834;

15. Farinelli, S. E. and L. A. Greene (1996) "Cell blockers mimosine, ciclopirox, and deferoxamine prevent the death of PC12 cells and postmitotic sympathetic neurons after removal of trophic support." *J. Neurosci.* 16: 1150–1162;

16. Farrow, S. N., et al. (1995) "Cloning of a bcl-2 homologue by interaction with adenovirus E1B 19K." *Nature* 374: 731–733;

17. Fernandez-Sarabia, M. J., et al. (1993) "Bcl-2 associates with the ras-related protein R-ras p23." *Nature* 366: 274–275;

18. Freeman, R. S., et al. (1994) "Analysis of cell cycle related gene expression in post-mitotic neurons: selective induction of cyclin D1 during prrammed cell death." *Neuron* 12: 343–355;

19. Friedman, L. S., et al. (1995) "Twenty-two genes from chromosome 17q21: cloning, sequencing and characterization of mutations in breast cancer families and tumors." *Genomics* 25: 256–263;

20. Friedman, L. S., et al. (1994) "The search for BRCA1." *Cancer Res.* 54: 6374–6382;

21. Futreal, P. A., et al. (1994) "BRCA1 mutations in primary breast and ovarian carcinomas." *Science* 266: 120–122;

22. Futreal, P. A., et al. "Detection of frequent allelic loss on proximal chromosome 17q in sporadic breast carcinoma using microsatellite length polymorphisms." *Cancer Res.* 52: 2624–2627;

23. Hall, J. M., et al. (1990) "Linkage of early-onset breast cancer to chromosome 17q21." *Science* 250: 1684–1689;

24. Hanada, M., et al. (1995) "Structure-function analysis of the Bcl-2 protein." *J. Biol. Chem.* 270: 11962–11969;

25. Hockenbery, D., et al. (1993) "Bcl-2 functions in an antioxidant pathway to prevent apoptosis." *Cell.* 75:241–251;

26. Hosking, L., et al. (1995) "A somatic BRCA1 mutation in an ovarian tumour." *Nature Genet* 9: 343–344;

27. Jacks, T., et al. (1992) "Effects of an Rb mutation in the mouse." *Nature* 359: 295–300;

28. Kane, D. J., et al. (1993) "Bcl-2 inhibition of neural cell death: Decreased generation of reactive oxygen species." *Science.* 262:1274–1276.

29. Kiefer, M. C., et al. (1995) "Modulation of apoptosis by the widely distributed Bcl-2 homologue Bak." *Nature* 374: 736–739;

30. King, K. L. and Cidlowski, J. A. (1995) "Cell cycle and apoptosis: common pathways to life and death." *J. Cell. Biochem.* 58: 175–180;

31. Lam, M. et al. (1994) "Evidence that Bcl-2 represses apoptosis by regulating endoplasmic reticulum-associated $Ca^{2+}$ fluxes." *Proc Natl Acad Sci USA* 91:6569–6573.

32. Lee, E-H, et al. (1992) "Mice deficient for Rb are nonviable and show defects in neurogenesis and haematopoiesis." *Nature* 359: 288–294;

33. Levine, B., et al. (1993) "Conversion of lytic to persistent alphavirus infection by the bcl-2 cellular oncogene." *Nature* 361: 739–742;

34. Lupas, A., et al. (1991) "Predicting Coiled Coils from Protein Sequences." *Science* 252: 1162–1164;

35. Matzel, S., et al. (1996) "Regulation of cell division cycle progression by bcl-2 expression; a potential mechanism for inhibition of programmed cell death." *J. Exp. Med.* 183: 2219–2226;

36. Miura, M., et al. (1993) Induction of apoptosis in fibroblasts by IL-1B converting enzyme, a mammalian homolog of the *C. elegans* cell death gene ced-2. *Cell* 75:653–660;

37. Merajver, S. D., et al. (1995) "Somatic mutations in the BRCA1 gene in sporadic ovarian tumors." *Nature Genet.* 9: 439–443;

38. Miki, Y., et al. (1994) "A strong candidate gene for the breast and ovarian cancer susceptibility gene BRCA1." *Science* 266: 66–71;

39. Oltvai, Z., et al. (1993) "Bcl-2 heterodimerizes in vivo with a conserved homolog, Bax, that accelerates programed cell death." *Cell* 74: 609–619;

40. Park, J. R., and Hockenberry, D. M. (1996) "Bcl-2, a novel regulator of apoptosis." *J. Cell. Biochem.* 60: 12–17;

41. Qin, X., et al. (1994) "Deregulated transcription factor E2F-1 expression leads to S-phase entry and p53-mediated apoptosis." *Proc Natl Acad Sci USA* 91: 10918–10922;

42. Reed, J. C., et al. (1990) "Bcl-2 family proteins; regulators of cell death involved in the pathogenesis of cancer and resistance to therapy." *J. Cell. Biochem.* 60: 23–32;

43. Rommens, J. M., et al. (1995) "Generation of a transcription map at the HSD17B locus centromeric to BRCA1 at 17q21." *Genomics* 28: 530–542;

44. Russell, S. E. H., et al. (1990) "Allele loss from chromosome 17 in ovarian cancer." *Oncogene* 5: 1581–1583;

45. Sambrook, et al. (1989) Molecular Cloning—A Laboratory Manual, 2nd Edition, Cold Spring Harbor Laboratory Press.

46. Saito, H., et al. (1993) "Detailed deletion mapping of chromosome 17q in ovarian and breast cancers: 2-cM region on 17q21.1 often and commonly deleted in tumors." *Cancer Res.* 53: 3382–3385;

47. Sato, T., et al. (1994) "Interactions among members of the Bcl-2 protein family analyzed with a yeast two-hybrid system." *Proc. Natl. Acad. Sci USA* 91: 9238–9242;

48. Sedlak, T. W., et al. (1995) "Multiple Bcl-2 family members demonstrate selective dimerizations with Bax." *Proc. Natl. Acad. Sci.* USA 92: 7834–7838;

49. Soares, M. B., et. al. (1994) "Construction and characterization of a normalized cDNA library." *Proc. Natl. Acad. Sci USA* 91: 9228–9232;

50. Shan, B. and Lee, W. H. (1994) "Deregulated expression of E2F-1 induces S-phase entry and leads to apoptosis." *Mol Cell Biol* 14: 8166–8173;

51. Shi, L., et al. (1994) "Premature $p34^{cdc2}$ activation required for apoptosis." *Science* 263: 1143–1145;

52. Szabo, C. I. and King, M. C. (1996) "Inherited breast cancer and ovarian cancer." *Hum. Mol. Genet.* 4 review: 1811–1817;

53. Takhashi, H., et al. (1995) "Mutation analysis of the BRCA1 gene in ovarian cancers." *Cancer Res.* 55: 2998–3002;

54. Takayama, S., et al. (1995) "Cloning and functional analysis of BAG-1: a novel Bcl-2-binding protein with anti-cell death activity." *Cell* 80: 279–284;

55. Tanaka, N., et al. (1994) "Cellular commitment to oncogene-induced transformation or apoptosis is dependent on the transcription factor IRF-1." *Cell* 77: 829–839;

56. Tangir, J., et al. (1996) "A 400 kb novel deletion unit centromeric to the BRCA1 gene in sporadic epithelial ovarian cancer." *Oncogene* 12: 735–740;

57. Tsujimoto, Y., et al. (1985) "Involvement of the bcl-2 gene in human follicular lymphoma." *Science* 228: 1440–1443;

58. Wang, H-G., et al. (1994) Apoptosis regulation by interaction of Bcl-2 protein and Raf-1 kinase. *Oncogene* 90: 2751–2756.

59. White, E., et al. (1991) "Adenovirus E1B 19-kilodalton protein overcomes the cytotoxicity of E1A proteins." *J. Virol.* 65: 2968–2978;

60. Wyllie, A. H., et al. (1987) "Rodent fibroblast tumors expressing human myc and ras genes: Growth, metastasis and endogenous oncogene expression." *Br. J. Cancer* 56: 251–259;

61. Wu, X., and Levine, A. J. (1994) "p53 and E2F-1 cooperate to mediate apoptosis." *Proc Natl. Acad Sci USA* 91: 3602–3606;

62. Yan-Feng, et al. (1993) "Allelic loss in ovarian cancer." *Int. J. Cancer* 54: 546–551;

63. Yang, E., et al. (1995) "Bad, a heterodimeric partner for Bclxl and Bcl-2, displaces Bax and promotes cell death." *Cell* 80: 285–291;

64. Yin, X. M., et al. (1994) "BH1 and BH2 domains of Bcl-2 are required for inhibition of apoptosis and heterodimerization with BAX." *Nature* 369: 321–323.

What is claimed is:

1. A method for identifying a subject with a predisposition for cancer, comprising:
   a. obtaining a nucleic acid sample from the subject; and
   b. determining whether the nucleic acid which in wildtype form encodes human Beclin is encoding a polypeptide having no cellular proliferation inhibition activity or reduced cellular proliferation inhibition activity, wherein no cellular proliferation inhibition activity or reduced cellular proliferation inhibition activity indicates a predisposition to cancer.

2. The method of claim 1, wherein the determining of step b comprises: determining whether the nucleic acid which in wildtype form encodes a human Beclin contains a premature stop codon, wherein a premature stop codon indicates a predisposition to cancer.

3. The method of claim 1, wherein the nucleic acid sample in step (a) comprises mRNA.

4. The method of claim 2, wherein the nucleic acid sample in step (a) comprises mRNA.

5. The method of claim 1, wherein the determining of step (b) comprises:
   i. producing a protein from the nucleic acid sample of step (a); and
   ii. comparing the protein of step (i) with wildtype human Beclin.

6. The method of claim 1, wherein the determining of step (b) comprises:
   i. producing a protein from the nucleic acid sample of step (a); and
   ii. assessing the protein of step (i) for its ability to restore cellular proliferation inhibition activity to a cell having no Beclin or reduced levels of Beclin.

7. A method of detecting a nucleic acid encoding a mutant human beclin comprising:
   (a) hybridizing the nucleic acid with a probe consisting of a nucleic acid which encodes SEQ ID NO 1,
   (b) isolating the nucleic acid obtained by hybridization,
   (c) determining the nucleotide sequence of the isolated nucleic acid, and
   (d) comparing the nucleotide sequence of the isolated nucleic acid with a nucleotide sequence which encodes SEQ ID NO 1 in order to identify a mutant human beclin.

8. A method of detecting a nucleic acid encoding a mutant human beclin comprising:
   (a) hybridizing the nucleic acid with a probe consisting of the nucleotide sequence of SEQ ID NO 2,
   (b) isolating the nucleic acid obtained by hybridization,
   (c) determining the nucleotide sequence of the isolated nucleic acid, and
   (d) comparing the nucleotide sequence of the isolated nucleic acid with the nucleotide sequence of SEQ ID NO 2 in order to identify a mutant human beclin.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 450 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

```
Met Glu Gly Ser Lys Thr Ser Asn Asn Ser Thr Met Gln Val Ser Phe
 1               5                  10                  15
Val Cys Gln Arg Cys Ser Gln Pro Leu Lys Leu Asp Thr Ser Phe Lys
                20                  25                  30
Ile Leu Asp Arg Val Thr Ile Gln Glu Leu Thr Ala Pro Leu Leu Thr
                35                  40                  45
Thr Ala Gln Ala Lys Pro Gly Glu Thr Gln Glu Glu Thr Asn Ser
        50                  55                  60
Gly Glu Glu Pro Phe Ile Glu Thr Pro Arg Gln Asp Gly Val Ser Arg
 65                      70                  75                  80
Arg Phe Ile Pro Pro Ala Arg Met Met Ser Thr Glu Ser Ala Asn Ser
                85                  90                  95
Phe Thr Leu Ile Gly Glu Val Ser Asp Gly Gly Thr Met Glu Asn Leu
               100                 105                 110
Ser Arg Arg Leu Lys Val Thr Gly Asp Leu Phe Asp Ile Met Ser Gly
               115                 120                 125
Gln Thr Asp Val Asp His Pro Leu Cys Glu Glu Cys Thr Asp Thr Leu
        130                 135                 140
Leu Asp Gln Leu Asp Thr Gln Leu Asn Val Thr Glu Asn Glu Cys Gln
145                 150                 155                 160
Asn Tyr Lys Arg Cys Leu Glu Ile Leu Glu Gln Met Asn Glu Asp Asp
                165                 170                 175
Ser Glu Gln Leu Gln Met Glu Leu Lys Glu Leu Ala Leu Glu Glu Glu
        180                 185                 190
Arg Leu Ile Gln Glu Leu Glu Asp Val Glu Lys Asn Arg Lys Ile Val
        195                 200                 205
Ala Glu Asn Leu Glu Lys Val Gln Ala Glu Ala Glu Arg Leu Asp Gln
210                 215                 220
Glu Glu Ala Gln Tyr Gln Arg Glu Tyr Ser Glu Phe Lys Arg Gln Gln
225                 230                 235                 240
Leu Glu Leu Asp Asp Glu Leu Lys Ser Val Glu Asn Gln Met Arg Tyr
                245                 250                 255
Ala Gln Thr Gln Leu Asp Lys Leu Lys Lys Thr Asn Val Phe Asn Ala
        260                 265                 270
Thr Phe His Ile Trp His Ser Gly Gln Phe Gly Thr Ile Asn Asn Phe
            275                 280                 285
Arg Leu Gly Arg Leu Pro Ser Val Pro Val Glu Trp Asn Glu Ile Asn
        290                 295                 300
```

```
Ala  Ala  Trp  Gly  Gln  Thr  Val  Leu  Leu  Leu  His  Ala  Leu  Ala  Asn  Lys
305                      310                      315                      320

Met  Gly  Leu  Lys  Phe  Gln  Arg  Tyr  Arg  Leu  Val  Pro  Tyr  Gly  Asn  His
                    325                      330                      335

Ser  Tyr  Leu  Glu  Ser  Leu  Thr  Asp  Lys  Ser  Lys  Glu  Leu  Pro  Leu  Tyr
                    340                      345                      350

Cys  Ser  Gly  Gly  Leu  Arg  Phe  Phe  Trp  Asp  Asn  Lys  Phe  Asp  His  Ala
               355                      360                      365

Met  Val  Ala  Phe  Leu  Asp  Cys  Val  Gln  Gln  Phe  Lys  Glu  Glu  Val  Glu
               370                      375                      380

Lys  Gly  Glu  Thr  Arg  Phe  Cys  Leu  Pro  Tyr  Arg  Met  Asp  Val  Glu  Lys
385                      390                      395                      400

Gly  Lys  Ile  Glu  Asp  Thr  Gly  Gly  Ser  Gly  Gly  Ser  Tyr  Ser  Ile  Lys
                    405                      410                      415

Thr  Gln  Phe  Asn  Ser  Glu  Glu  Gln  Trp  Thr  Lys  Ala  Leu  Lys  Phe  Met
               420                      425                      430

Leu  Thr  Asn  Leu  Lys  Trp  Gly  Leu  Ala  Trp  Val  Ser  Ser  Gln  Phe  Tyr
          435                      440                      445

Asn  Lys
450
```

( 2 ) INFORMATION FOR SEQ ID NO:2:

( i ) SEQUENCE CHARACTERISTICS:
        ( A ) LENGTH: 1353 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:2:

```
ATGGAAGGGT CTAAGACGTC CAACAACAGC ACCATGCAGG TGAGCTTCGT GTGCCAGCGC    60
TGCAGCCAGC CCCTGAAACT GGACACGAGT TTCAAGATCC TGGACCGTGT CACCATCCAG   120
GAACTCACAG CTCCATTACT TACCACAGCC CAGGCGAAAC CAGGAGAGAC CCAGGAGGAA   180
GAGACTAACT CAGGAGAGGA GCCATTTATT GAAACTCCTC GCCAGGATGG TGTCTCTCGC   240
AGATTCATCC CCCAGCCAG  GATGATGTCC ACAGAAAGTG CCAACAGCTT CACTCTGATT   300
GGGGAGGTAT CTGATGGCGG CACCATGGAG AACCTCAGCC GAAGACTGAA GGTCACTGGG   360
GACCTTTTTG ACATCATGTC GGGCCAGACA GATGTGGATC ACCCACTCTG TGAGGAATGC   420
ACAGATACTC TTTTAGACCA GCTGGACACT CAGCTCAACG TCACTGAAAA TGAGTGTCAG   480
AACTACAAAC GCTGTTTGGA GATCTTAGAG CAAATGAATG AGGATGACAG TGAACAGTTA   540
CAGATGGAGC TAAAGGAGCT GGCACTAGAG GAGGAGAGGC TGATCCAGGA GCTGGAAGAC   600
GTGGAAAAGA ACCGCAAGAT AGTGGCAGAA ATCTCGAGA  AGGTCCAGGC TGAGGCTGAG   660
AGACTGGATC AGGAGGAAGC TCAGTATCAG AGAGAATACA GTGAATTTAA ACGACAGCAG   720
CTGGAGCTGG ATGATGAGCT GAAGAGTGTT GAAAACCAGA TGCGTTATGC CCAGACGCAG   780
CTGGATAAGC TGAAGAAAAC CAACGTCTTT AATGCAACCT TCCACATCTG GCACAGTGGA   840
CAGTTTGGCA CAATCAATAA CTTCAGGCTG GGTCGCCTGC CCAGTGTTCC CGTGGAATGG   900
AATGAGATTA ATGCTGCTTG GGGCCAGACT GTGTTGCTGC TCCATGCTCT GGCCAATAAG   960
ATGGGTCTGA AATTTCAGAG ATACCGACTT GTTCCTTACG GAAACCATTC ATATCTGGAG  1020
```

```
TCTCTGACAG  ACAAATCTAA  GGAGCTGCCG  TTATACTGTT  CTGGGGGGTT  GCGGTTTTTC    1080

TGGGACAACA  AGTTTGACCA  TGCAATGGTG  GCTTTCCTGG  ACTGTGTGCA  GCAGTTCAAA    1140

GAAGAGGTTG  AGAAAGGCGA  GACACGTTTT  TGTCTTCCCT  ACAGGATGGA  TGTGGAGAAA    1200

GGCAAGATTG  AAGACACAGG  AGGCAGTGGC  GGCTCCTATT  CCATCAAAAC  CCAGTTTAAC    1260

TCTGAGGAGC  AGTGGACAAA  AGCTCTCAAG  TTCATGCTGA  CGAATCTTAA  GTGGGGTCTT    1320

GCTTGGGTGT  CCTCACAATT  TTATAACAAA  TGA                                  1353
```

( 2 ) INFORMATION FOR SEQ ID NO:3:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i i ) HYPOTHETICAL: NO ( i v ) ANTI-SENSE: NO ( x i ) SEQUENCE DESCRIPTION: SEQ ID NO:3:

```
Glu  Leu  Phe  Arg  Asp  Gly  Val  Asn  Trp  Gly  Arg  Ile  Val  Ala  Phe  Phe
 1                    5                        10                         15
Glu  Phe  Gly  Gly
              20
```

( 2 ) INFORMATION FOR SEQ ID NO:4:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i i ) HYPOTHETICAL: NO ( i v ) ANTI-SENSE: NO ( x i ) SEQUENCE DESCRIPTION: SEQ ID NO:4:

```
Glu  Leu  Phe  Arg  Asp  Gly  Val  Asn  Trp  Gly  Arg  Ile  Val  Ala  Phe  Phe
 1                    5                        10                         15
Ser  Phe  Gly  Gly
              20
```

( 2 ) INFORMATION FOR SEQ ID NO:5:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i i ) HYPOTHETICAL: NO ( i v ) ANTI-SENSE: NO ( x i ) SEQUENCE DESCRIPTION: SEQ ID NO:5:

```
Glu  Leu  Phe  Arg  Asp  Gly  Val  Asn  Trp  Ala  Arg  Ile  Val  Ala  Phe  Phe
 1                    5                        10                         15
Glu  Phe  Gly  Gly
              20
```

( 2 ) INFORMATION FOR SEQ ID NO:6:

( i ) SEQUENCE CHARACTERISTICS:
    ( A ) LENGTH: 20 amino acids

```
    ( B ) TYPE: amino acid
    ( C ) STRANDEDNESS: single
    ( D ) TOPOLOGY: linear ( i i i ) HYPOTHETICAL: NO ( i v ) ANTI-SENSE: NO ( x i ) SEQUENCE DESCRIPTION: SEQ ID NO:6:

Glu  Leu  Phe  Arg  Asp  Gly  Ala  Ile  Leu  Gly  Arg  Ile  Val  Ala  Phe  Phe
 1                    5                        10                         15

Ser  Phe  Gly  Gly
             20
```